US009977135B2

(12) United States Patent
Yokoyama et al.

(10) Patent No.: US 9,977,135 B2
(45) Date of Patent: May 22, 2018

(54) RADIATION IMAGING APPARATUS AND RADIATION DETECTION SYSTEM

(71) Applicant: CANON KABUSHIKI KAISHA, Tokyo (JP)

(72) Inventors: Keigo Yokoyama, Honjo (JP); Minoru Watanabe, Honjo (JP); Masato Ofuji, Takasaki (JP); Jun Kawanabe, Kumagaya (JP); Kentaro Fujiyoshi, Tokyo (JP); Hiroshi Wayama, Honjo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 255 days.

(21) Appl. No.: 14/817,301

(22) Filed: Aug. 4, 2015

(65) Prior Publication Data

US 2016/0047920 A1    Feb. 18, 2016

(30) Foreign Application Priority Data

Aug. 12, 2014 (JP) .................................. 2014-164530

(51) Int. Cl.
*H05G 1/56* (2006.01)
*G01T 1/24* (2006.01)
(Continued)

(52) U.S. Cl.
CPC ............ *G01T 1/247* (2013.01); *A61B 6/4233* (2013.01); *A61B 6/54* (2013.01); *G01N 23/04* (2013.01);
(Continued)

(58) Field of Classification Search
CPC .......... G01N 23/04; G01T 1/026; G01T 1/247
(Continued)

(56) References Cited

U.S. PATENT DOCUMENTS 7,408,167 B2    8/2008  Kameshima et al. ... 250/370.09
7,514,663 B2    4/2009  Yagi et al. ................. 250/208.1
(Continued)

FOREIGN PATENT DOCUMENTS

CN    102170828    8/2011
CN    102961156    3/2013
(Continued)

OTHER PUBLICATIONS

U.K. Search and Examination Report dated Mar. 16, 2016 in U.K. counterpart application 1514179.9 (in English).
(Continued)

*Primary Examiner* — Courtney Thomas
(74) *Attorney, Agent, or Firm* — Fitzpatrick Cella Harper and Scinto

(57) ABSTRACT

A radiation imaging apparatus comprises a sensor portion including a pixel array configured to acquire an image signal corresponding to radiation, and a plurality of detection elements arranged in the pixel array and configured to detect the radiation, and a readout circuit configured to read out the image signal from the sensor portion, wherein the readout circuit includes a signal processing circuit arranged to combine and process signals from the plurality of detection elements if determining the presence or absence of radiation irradiation, and to process a signal for each detection element or combine and process signals from a number of detection elements from among the plurality of detection elements, the number being less than the number of detection elements that include the plurality of detection elements, if determining a radiation dose.

9 Claims, 16 Drawing Sheets

(51) Int. Cl.
*G01N 23/04* (2018.01)
*G01T 1/02* (2006.01)
*G01T 1/17* (2006.01)
*H04N 5/32* (2006.01)
*A61B 6/00* (2006.01)

(52) U.S. Cl.
CPC .............. *G01T 1/023* (2013.01); *G01T 1/026* (2013.01); *G01T 1/17* (2013.01); *H04N 5/32* (2013.01)

(58) Field of Classification Search
USPC ............... 378/62, 98.8; 250/370.07, 370.08, 250/370.09, 370.11
See application file for complete search history.

(56) References Cited

U.S. PATENT DOCUMENTS

| | | | |
|---|---|---|---|
| 7,541,591 B2 | 6/2009 | Endo et al. | 250/369 |
| 7,629,587 B2 | 12/2009 | Yagi et al. | 250/370.15 |
| 7,718,973 B2 | 5/2010 | Endo et al. | 250/370.08 |
| 7,732,778 B2 | 6/2010 | Yokoyama et al. | 250/370.08 |
| 7,989,772 B2 | 8/2011 | Yagi et al. | 250/370.09 |
| 8,107,588 B2 | 1/2012 | Kameshima et al. | 378/62 |
| 8,723,996 B2 | 5/2014 | Yokoyama et al. | 348/294 |
| 8,829,348 B2 | 9/2014 | Sato et al. | 250/336.1 |
| 8,983,035 B2* | 3/2015 | Noma | H05G 1/64 250/214 DC |
| 2011/0317054 A1 | 12/2011 | Kameshima et al. | 348/302 |
| 2012/0001079 A1 | 1/2012 | Okada | 250/366 |
| 2012/0001082 A1* | 1/2012 | Shoho | G01T 1/00 250/369 |
| 2013/0136234 A1* | 5/2013 | Noma | H05G 1/64 378/91 |
| 2013/0320224 A1* | 12/2013 | Sato | A61B 6/5205 250/394 |
| 2014/0086391 A1 | 3/2014 | Ohta et al. | 378/91 |
| 2015/0164458 A1* | 6/2015 | Tajima | A61B 6/4283 378/97 |

FOREIGN PATENT DOCUMENTS

| | | |
|---|---|---|
| CN | 103126695 | 6/2013 |
| CN | 104641257 | 5/2015 |
| EP | 2564782 | 3/2013 |
| EP | 2623032 | 8/2013 |
| JP | 2006-334154 | 12/2006 |
| JP | 2012-015913 | 1/2012 |
| JP | 2014-068882 | 4/2014 |
| WO | 2012/082276 A | 6/2012 |
| WO | 2014/038480 | 3/2014 |

OTHER PUBLICATIONS

Search Report issued on Dec. 19, 2016, in counterpart Russian patent application 2015132748 (in English).
U.S. Appl. No. 14/696,976, filed Apr. 27, 2015.
U.S. Appl. No. 14/721,122, filed May 26, 2015.
U.S. Appl. No. 14/729,248, filed Jun. 3, 2015.
U.S. Appl. No. 14/802,297, filed Jul. 17, 2015.

* cited by examiner

F I G. 11
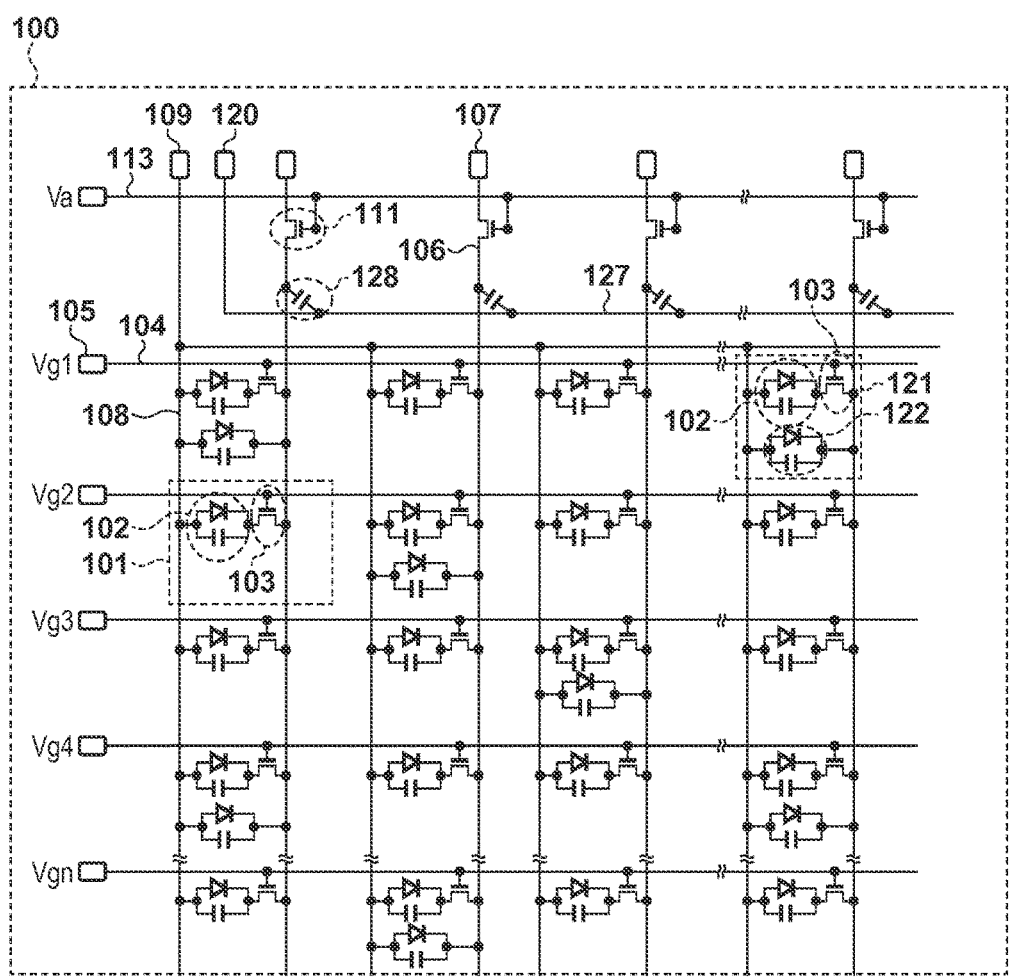

RADIATION IMAGING APPARATUS AND RADIATION DETECTION SYSTEM

BACKGROUND OF THE INVENTION

Field of the Invention

The present invention relates to a radiation imaging apparatus and a radiation detection system.

Description of the Related Art

As an imaging apparatus used for medical imaging diagnosis or nondestructive inspection by X-rays, a radiation imaging apparatus has been put to practical use, which uses a matrix substrate including a pixel array formed by combining switch elements such as TFTs (Thin Film Transistors) and conversion elements such as photoelectric conversion elements. Such a radiation imaging apparatus often performs an imaging operation in synchronism with radiation irradiation by a radiation generator. Synchronization is done mainly at two timings. The first timing is the timing of detecting radiation irradiation by the radiation generator and the start of the accumulation operation of the radiation imaging apparatus. Japanese Patent Laid-Open No. 2012-15913 discloses a radiation detection element capable of detecting the presence/absence of radiation irradiation without using a synchronization signal. When notified of change to the imaging mode, the radiation imaging apparatus transits from a standby state to a radiation detection wait state and determines the presence/absence of radiation irradiation.

The second timing is the timing of generating a radiation irradiation stop instruction to the radiation generator corresponding to the cumulative exposure dose of radiation from the radiation generator to a sensor. A device configured to do synchronization with these timings is called AEC (Automatic Exposure Control) that controls a radiation transmission dose. Japanese Patent Laid-Open No. 2006-334154 discloses correcting a radiation dose using signals from the pixels of an ROI (Region Of Interest) obtained by fluorography to attain a clear X-ray image.

To detect the start of irradiation of radiation from the radiation generator, it is necessary to continuously monitor the signal from the radiation detection element, as described in Japanese Patent Laid-Open No. 2012-15913. More specifically, to detect the signal output from the radiation detection element, the circuit used to determine the presence/absence of radiation irradiation needs to be continuously operated for a time of several sec to several min. In addition, to detect the radiation exposure dose (radiation dose) in the region of interest (ROI), processing needs to be performed for each ROI, as described in Japanese Patent Laid-Open No. 2006-334154. In a case where a single detection element serves as the detection element for detecting the presence/absence of radiation irradiation and the detection element for detecting the radiation exposure dose in the ROI, if the arrangement of detection elements is optimized to determine the presence/absence of radiation irradiation, the spatial resolution may be short when detecting the radiation dose. On the other hand, if the arrangement of detection elements is optimized to determine the radiation dose, the number of ROIs increases, and the outputs from the detection elements disperse for each ROI, and it may be impossible to sufficiently obtain a signal level to determine the start of radiation irradiation.

SUMMARY OF THE INVENTION

According to an aspect of the present invention, the present invention provides a radiation imaging apparatus for determining the presence or absence of radiation irradiation and determining a radiation dose, the radiation imaging apparatus including a sensor portion including a pixel array configured to acquire an image signal indicating detected radiation, and a plurality of detection elements arranged in the pixel array and configured to detect the radiation and a readout circuit configured to read out the image signal from the sensor portion, wherein the readout circuit includes a signal processing circuit arranged to combine and process signals from the plurality of detection elements if determining the presence or absence of radiation irradiation, and to process a signal for each detection element or combine and process signals from a number of detection elements from among the plurality of detection elements, the number being less than the number of detection elements that include the plurality of detection elements, if determining a radiation dose.

Further features of the present invention will become apparent from the following description of embodiments with reference to the attached drawings.

BRIEF DESCRIPTION OF THE DRAWINGS

FIG. 11 is a circuit diagram showing an arrangement of a modification of the radiation imaging apparatus according to the third embodiment of the present invention;

DESCRIPTION OF THE EMBODIMENTS

Figure 1:
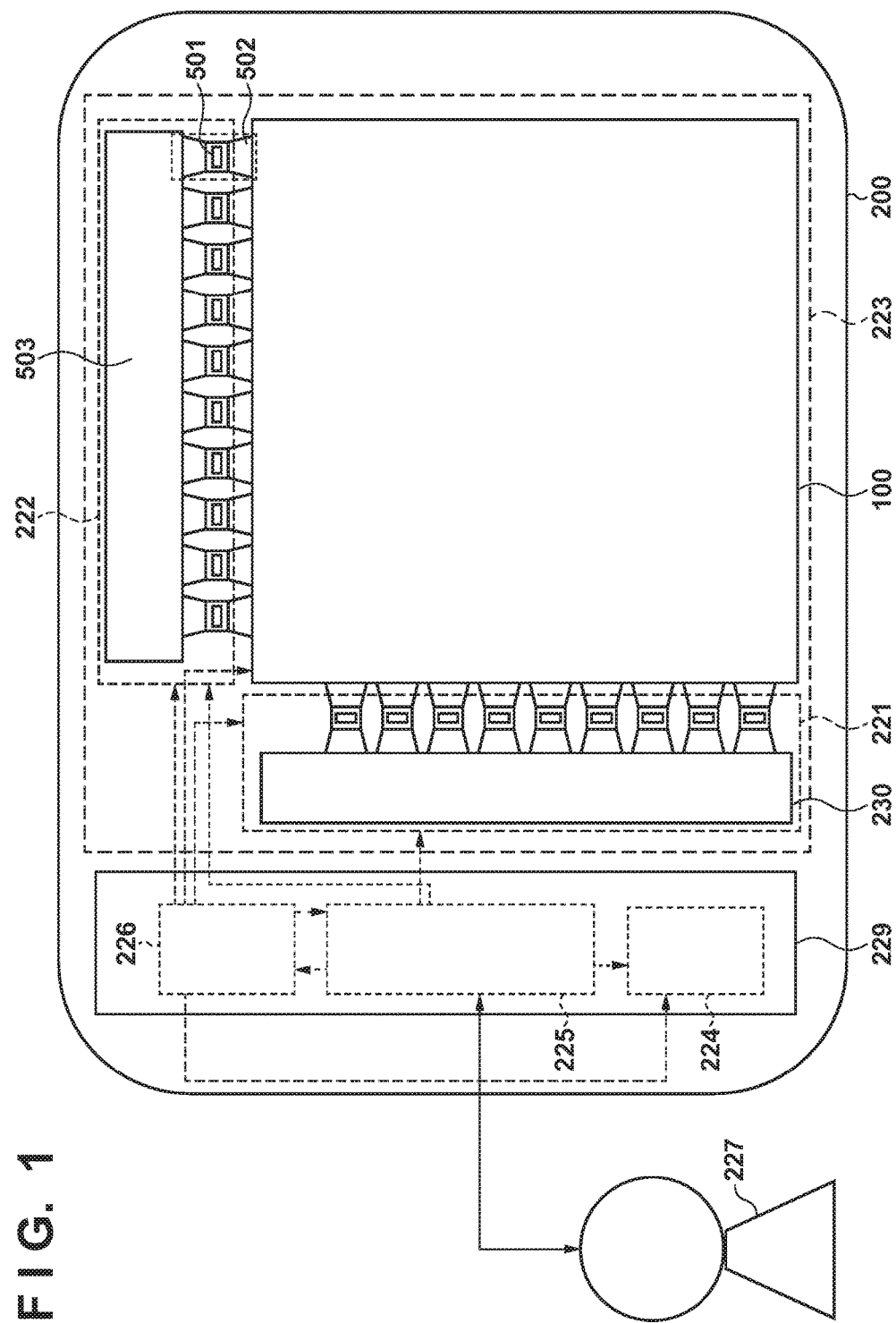
FIG. 1 is a view showing an example of an arrangement of a radiation imaging apparatus.

First Embodiment (a) Arrangement of Radiation Imaging Apparatus

An arrangement of a radiation imaging apparatus according to this embodiment will be described with reference to FIGS. 1 to 5C. A radiation imaging apparatus 200 includes a support substrate 100 on which a sensor portion including at least a first pixel 101 and a second pixel (detecting pixel) 121 is mounted. The second pixel is a detecting pixel. The first pixel 101 is a pixel that outputs a signal to be converted into a radiation image, and includes a conversion element 102 and a switch element 103. The detecting pixel 121 is a pixel that outputs a signal used to determine the presence/absence (i.e. the presence or absence) of radiation irradiation and determine the radiation exposure dose (radiation dose) in addition to a signal to be converted into a radiation image. The detecting pixel 121 includes a detection element 122 and a switch element 123 for the detection element in addition to the conversion element 102 and the switch element 103. The radiation imaging apparatus 200 includes a detection portion 223 including a driving circuit 221 that drives the sensor portion, and a readout circuit 222 that outputs an electrical signal from the sensor portion as image data. The driving circuit 221 controls the selected state and unselected state of each switch element arranged in the support substrate 100.

Figure 2:
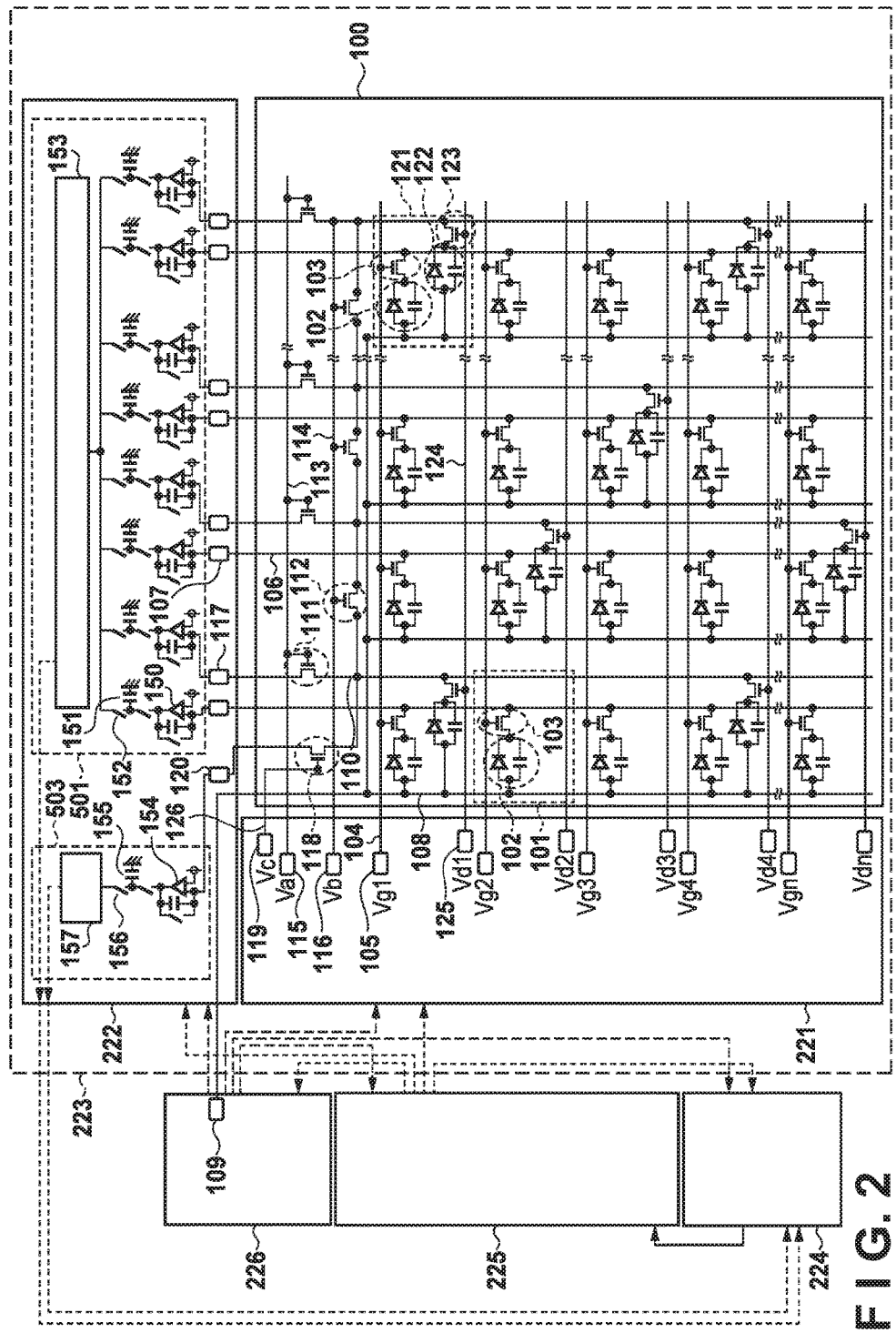
FIG. 2 is a circuit diagram showing an arrangement of a radiation imaging apparatus according to a first embodiment of the present invention.

As shown in FIG. 2, the readout circuit 222 includes image signal input terminals 107, a first signal input terminal 120, and second signal input terminals 117. The readout circuit 222 includes a first signal processing circuit that operates when determining the presence/absence of radiation irradiation, and a second signal processing circuit that operates when determining the radiation dose. More specifically, in the readout circuit 222, the image signal input terminal 107 or the second signal input terminal 117 is connected to the inverting input terminal of each operational amplifier 150. The inverting input terminal of the operational amplifier 150 or 154 is connected to the output terminal via a feedback capacitor, and the non-inverting input terminal is connected to an arbitrary fixed potential so that the circuit functions as a charge-voltage converter. An A/D converter 153 is connected to the subsequent stage of the operational amplifiers 150 via sample hold circuits 151 and multiplexers 152. Signal charges from the image signal input terminals 107 and the second signal input terminals 117 are converted into a digital signal by the A/D converter 153. Similarly, in the readout circuit 222, the first signal input terminal 120 is connected to the inverting input terminal of the operational amplifier 154. An A/D converter 157 is connected to the subsequent stage of the operational amplifier 154 via a sample hold circuit 155 and a multiplexer 156. Signal charges from the first signal input terminal 120 are converted into a digital signal by the A/D converter 157.

In this embodiment, the circuits configured to process signals are separated such that the outputs from the image signal input terminals 107 and the second signal input terminals 117 are processed by the A/D converter 153, and the output from the first signal input terminal 120 is processed by the A/D converter 157. In this embodiment, circuits from the first signal input terminal 120 to the A/D converter 157 correspond to the first signal processing circuit and are mounted on a printed board 503. Additionally, in this embodiment, circuits from the image signal input terminals 107 and the second signal input terminals 117 to the A/D converter 153 correspond to the second signal processing circuit and are mounted on an integrated circuit 501 placed on a flexible substrate 502. The second signal processing circuit individually processes signals from detection signal lines 110 and converts them into digital data. The radiation imaging apparatus 200 further includes a signal processing portion 224 that processes and outputs image data from the detection portion 223, and a control circuit 225 that supplies a control signal to each constituent element to control the operation of the detection portion 223. The radiation imaging apparatus 200 also includes a power supply circuit 226 that supplies a bias voltage and power to each circuit. The signal processing portion 224 receives information of an image signal line 106 or detection signal line 110 from the readout circuit 222, and sends the information to a control computer (not shown) or the control circuit 225. The control computer (not shown) or the control circuit 225 sends a control signal based on the information to the driving circuit 221 or an external radiation generator 227. Alternatively, the external radiation generator 227 may acquire the information of the control circuit 225 and control radiation generation.

The power supply circuit 226 includes a regulator circuit that receives power from an external power supply or internal battery (not shown) and supplies necessary power to the sensor portion, the driving circuit 221, the readout circuit 222, and the like. Note that although each of the driving circuit 221, the readout circuit 222, the signal processing portion 224, the control circuit 225, and the power supply circuit 226 is indicated by one block, this does not mean that each circuit is formed from one integrated circuit. Each circuit may be formed from a plurality of integrated circuits. Alternatively, all the circuits may be provided on one integrated circuit. The circuits are separated for the descriptive convenience. However, one circuit can serve as a plurality of circuits, or the circuits can separately be arranged. In the arrangement shown in FIG. 1, the signal processing portion 224, the control circuit 225, and the power supply circuit 226 are mounted on a printed board 229. The driving circuit 221 and the readout circuit 222 are provided on printed boards 230 and 503 and the flexible substrate 502, respectively. The printed boards 230 and 503 are connected to the sensor portion on the support substrate 100 via the flexible substrate 502. The above description can also be applied to other embodiments of the present invention as needed, as a matter of course.

(b) Circuit Arrangement

The arrangements of a pixel and a detecting pixel of the radiation imaging apparatus according to this embodiment will be described next. As shown in FIG. 2, a plurality of pixels and peripheral circuits are arranged in the radiation imaging apparatus according to this embodiment. The sensor portion including the pixel array with the plurality of pixels 101 and detecting pixels 121 arranged in a matrix is provided on the support substrate 100. Each pixel 101 is configured to output an electrical signal corresponding to radiation or light, and includes the conversion element 102 that converts radiation or light into charges, and the switch element 103 that outputs an electrical signal corresponding to the generated charges to a signal line. In this embodiment, the pixel 101 includes, as the conversion element 102, a scintillator that converts radiation into light, and a photoelectric conversion element that converts the light into charges. However, the present invention is not limited to this. A photoelectric conversion element that converts light converted by the scintillator into charges or a direct conversion element that directly converts radiation into charges may be used as the conversion element 102. The pixel 101 includes, as the switch element 103, a TFT (Thin Film Transistor) of amorphous silicon or polycrystalline silicon, and preferably uses a TFT of polycrystalline silicon. Silicon has been exemplified as the semiconductor material. However, the present invention is not limited to this, and another semiconductor material such as germanium may be used.

A first main electrode of the switch element 103 is electrically connected to a first electrode of the conversion element 102, and a bias line 108 is electrically connected to a second electrode of the conversion element 102. The bias line 108 is commonly connected to the second electrodes of the plurality of conversion elements 102 arranged along a column. The bias line 108 arranged on each column is commonly connected to bias lines arranged along rows and connected to a bias power supply terminal 109 of the power supply circuit 226 to receive a bias voltage. The image signal line 106 is electrically connected to the second main electrode of the switch element 103. The image signal line 106 is commonly connected to the second main electrodes of the switch elements 103 of the pixels arranged along a column. The image signal line 106 is arranged for each column of pixels. Each image signal line 106 is electrically connected to the image signal input terminal 107 of the external readout circuit 222.

A driving line 104 is electrically connected to the control electrode of the switch element 103 of the pixel 101. The driving line 104 is commonly connected to the control electrodes of the switch elements 103 of the pixels 101 arranged along a row. Gate control voltages Vg1 to Vgn are applied from the driving circuit 221 to the driving lines 104 via driving voltage terminals 105. The detecting pixel 121 is arranged in the pixel array. The detecting pixel 121 includes the conversion element 102 and the switch element 103 described above, and also includes the detection element 122 that detects radiation, and the switch element 123 connected to the detection element 122. The detection element 122 includes a scintillator that converts radiation into light, and a photoelectric conversion element that converts the light into charges. However, the present invention is not limited to this.

The first main electrode of the switch element 123 is connected to the first electrode of the detection element 122. The second electrodes of the detection elements 122 arranged along a column are connected to the bias line 108 arranged for each column. The detection signal line 110 arranged along a column is connected to the second main electrode of the switch element 123. A driving line 124 arranged for each row is connected to the control electrode of the switch element 123. Gate control voltages Vd1 to Vdn that control the switch elements 123 of the detection elements are applied from the driving circuit 221 to the driving lines 124 via driving voltage terminals 125. One or a plurality of detection elements are connected to each detection signal line 110 via the switch element 123. When the switch element 123 is turned on, a signal is output to the detection signal line 110 for each detection element connected to each driving line 124. Each detection signal line 110 is connected to the first main electrode of a switch element 111. The second main electrode of the switch element 111 is electrically connected to the external readout circuit 222 via the second signal input terminal 117. The control terminal of the switch element 111 is connected to a driving line 113 arranged along a row. A gate control voltage Va is applied from the driving circuit 221 to the driving line 113.

A switch element 112 is arranged between adjacent detection signal lines 110. The switch element 112 can connect the adjacent detection signal lines 110. Different detection signal lines 110 are connected to a first main electrode and a second main electrode of one switch element 112. A driving line 114 is connected to a control electrode of the switch element 112. A gate control voltage Vb is applied from the driving circuit 221 to the driving line 114.

A first main electrode of a switch element 118 is connected to some detection signal lines 110 in common with a first main electrode of the switch element 111. A second main electrode of the switch element 118 is electrically connected to a first signal input terminal 120 of the external readout circuit 222. A control electrode of the switch element 118 is connected to a driving line 126. A gate control voltage Vc that controls the control electrode is applied from the driving circuit 221 to the driving line 126 via a driving voltage terminal 119. The switch elements 111, 112, and 118 form part of a combining portion configured to combine the signals of the detection signal lines 110. In this embodiment, the image signal input terminals 107 and the second signal input terminals 117 of the readout circuit 222 are terminals that receive signals to obtain an image and signals to detect radiation from the conversion elements 102 and the detection elements 122.

(c) Detecting Pixel Structure

Figure 5A:
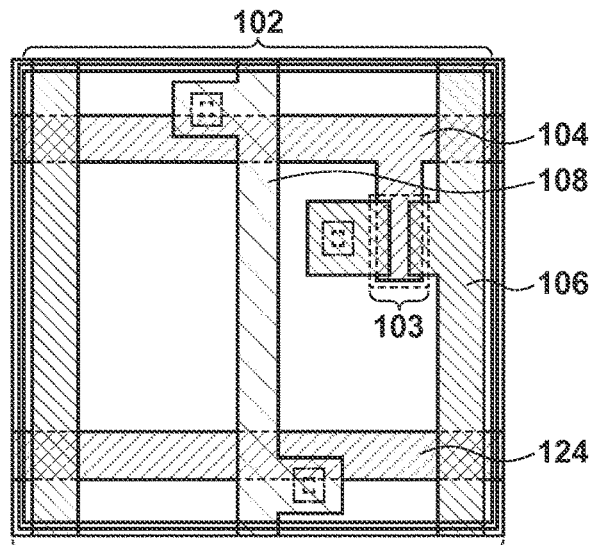
FIGS. 5A to 5C are views showing an example of arrangements of pixels of the radiation imaging apparatus according to the first embodiment of the present invention.
Figure 5B:
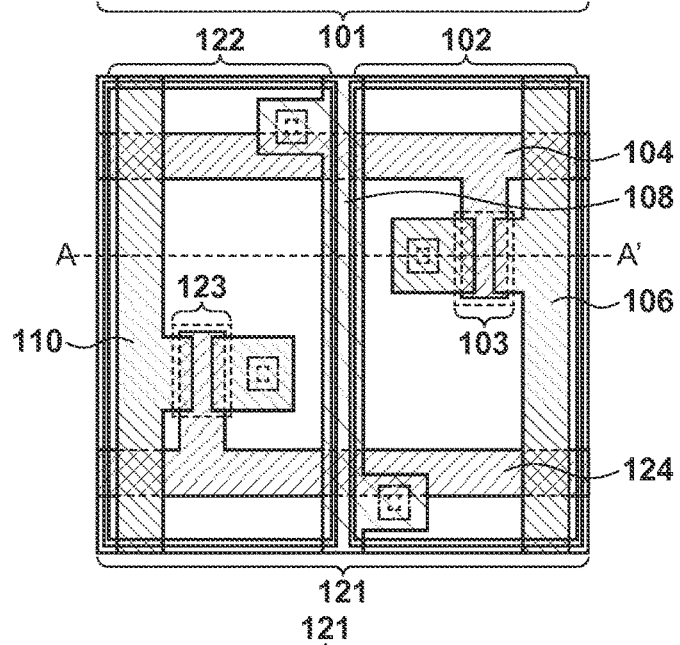

The structures of the pixels of the radiation imaging apparatus according to this embodiment will be described with reference to FIGS. 5A to 5C. FIG. 5A is a plan view of the pixel 101, and FIG. 5B is a plan view of the detecting pixel 121. The pixel 101 includes the conversion element 102 that converts radiation or light into charges, and the switch element 103 that is formed from a TFT and outputs an electrical signal corresponding to the charges of the conversion element 102. The detecting pixel 121 that outputs a radiation detection signal includes, as a portion configured to output an image signal, the conversion element 102 that converts radiation or light into charges, and the switch element 103 that is formed from a TFT and outputs an electrical signal corresponding to the charges of the conversion element 102. The detecting pixel 121 also includes the detection element 122 and the switch element 123.

Figure 5C:
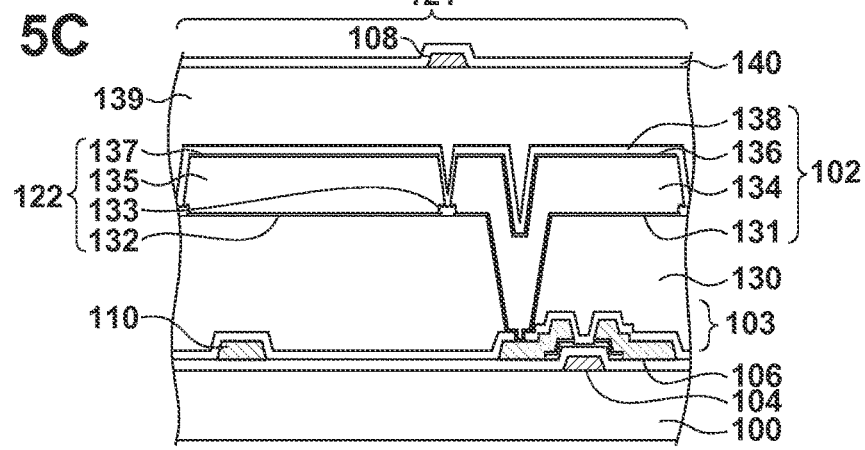

FIG. 5C is a sectional view taken along a line A-A' in FIG. 5B. In this embodiment, a PIN-type photodiode 134 is used as the conversion element 102. The conversion element 102 is stacked on an interlayer insulation film 130 on the switch element 103 provided on the insulating support substrate 100 which may be a glass substrate. The detecting pixel 121 includes, as a portion configured to output a detection signal, the detection element 122 that converts radiation or light into charges, and the switch element 123 that is formed from a TFT and outputs an electrical signal corresponding to the charges of the detection element 122. In this embodiment, a PIN-type photodiode 135 is used as the detection element 122. The detection element 122 is stacked on the interlayer insulation film 130 on the switch element 123 for the detection element provided on the insulating support substrate 100 which may be a glass substrate.

The conversion elements 102 and 122 are isolated to prevent their first electrodes 131 and 132 from being electrically connected. The insulating properties are enhanced by an insulation film 133 placed between the first electrodes 131 and 132 to insulate the elements. The above-described PIN-type photodiodes 134 and 135 are stacked on the first electrodes 131 and 132 and the insulation film 133 in the order of n-type layer-i-type layer-p-type layer. Second electrodes 136 and 137, a protective film 138, a second interlayer insulation film 139, the bias line 108, and a protective film 140 are sequentially arranged on the PIN-type photodiodes 134 and 135. A planarizing film and phosphor (neither are shown) are arranged on the protective film 140. Both the second electrodes 136 and 137 are connected to the bias line 108 via contacts formed in contact holes (not shown in FIG. 5C). ITO (Indium Tin Oxide) having optical transparency is used in the second electrodes 136 and 137 so that light converted from radiation by the phosphor (not shown) can transmit through them.

FIG. 5A is a plan view of the pixel 101 according to the present invention, which does not include the detection element 122 configured to output a detection signal, as compared to the pixel shown in FIG. 5B. The size of the conversion element 102 changes between the pixel 101 and the detecting pixel 121. For this reason, even if the amounts of radiation entering the pixels are the same, the amounts of output image signals are different. Hence, when a captured image is used for diagnosis, correction is performed to correct the variation in image signals.

(d) Operation

Figure 3:
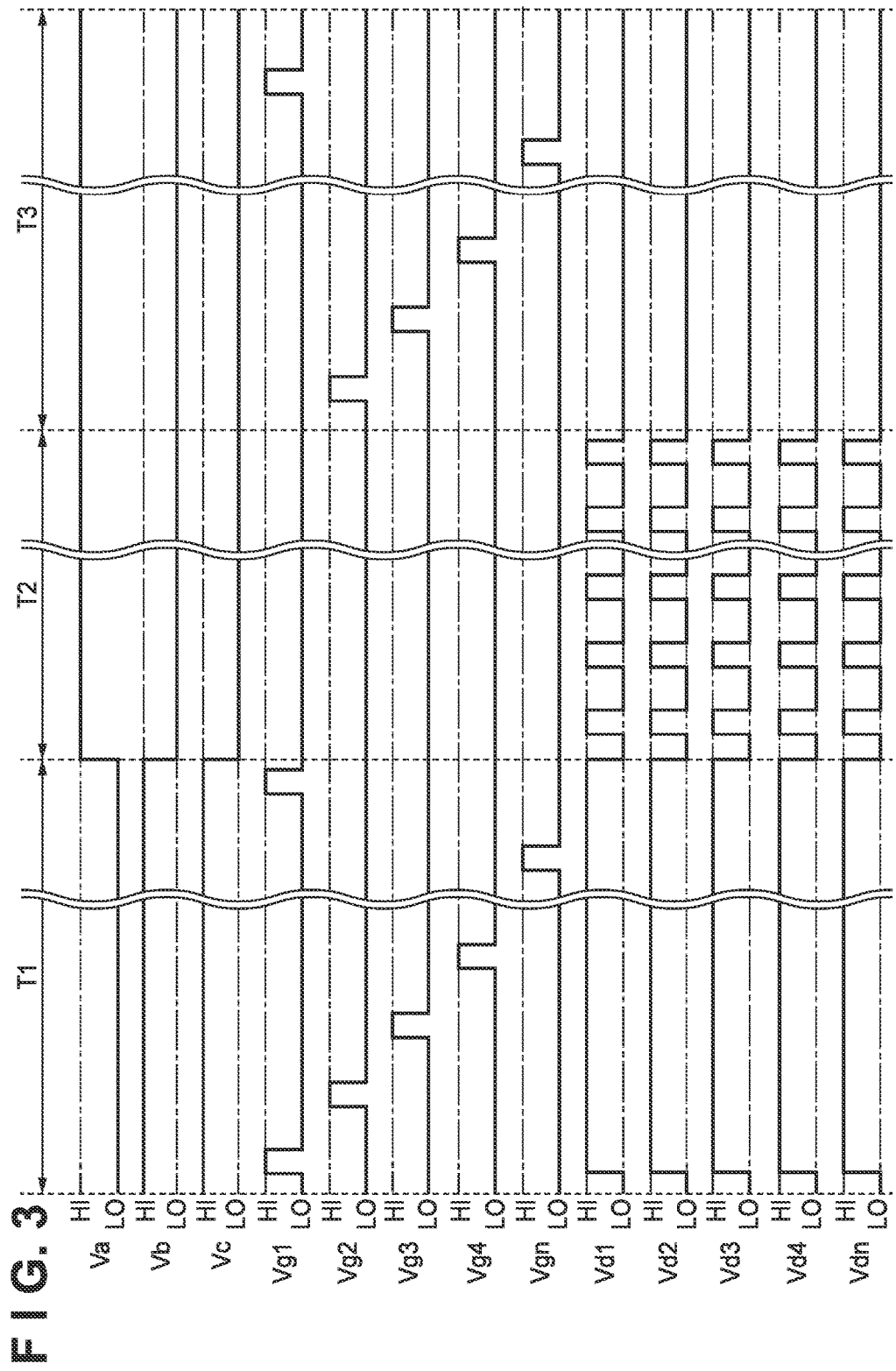
FIG. 3 is a timing chart of a radiation imaging apparatus according to the first embodiment of the present invention.
Figure 4:
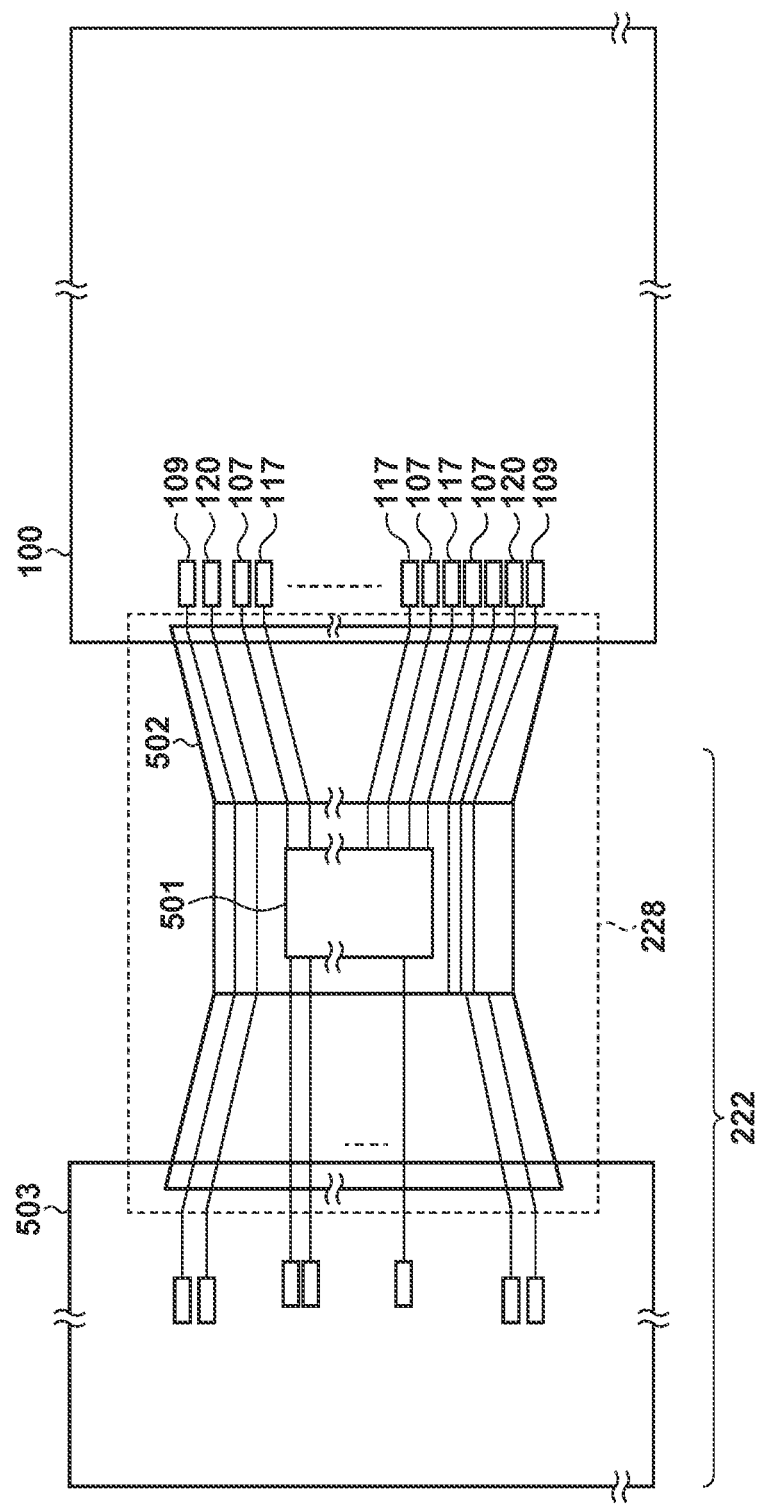
FIG. 4 is a view showing an example of connection between a readout circuit and a support substrate of the radiation imaging apparatus according to the first embodiment of the present invention.

The operation of the radiation imaging apparatus according to the first embodiment of the present invention will be described next with reference to FIGS. 2 and 3. In the following explanation, let Va, Vb, and Vc be the gate control voltages applied to the driving lines 113, 114, and 126, respectively. Let Vg1 to Vgn be the gate control voltages applied to the driving lines 104, and Vd1 to Vdn be the gate control voltages applied to the driving lines 124. Additionally, in FIG. 3, a voltage that changes each switch connected to each driving line to the ON state is expressed as HI, and a voltage that changes each switch to the OFF state is expressed as LO.

The operation in a period T1 shown in FIG. 3 will be described first. The period T1 is a period to detect the presence/absence of radiation irradiation. This period corresponds to, for example, the period after the radiation imaging apparatus is powered on to set a shooting enable state until the radiographer actually places an object in the radiation imaging apparatus and presses the radiation exposure switch to start radiation irradiation. During this period, the gate control voltages Vd1 to Vdn change to HI, and the switch elements 123 are set in the ON state. In addition, the gate control voltage Va is set to LO, and the gate control voltages Vb and Vc are set to HI. The switch elements 111 are turned off, and the switch elements 112 located between the detection signal lines 110 are turned on. At this time, the switch element 118 between the detection signal lines 110 and the first signal input terminal 120 is turned on. As a result, the plurality of detection elements 122 are electrically connected to the first signal input terminal 120. That is, the signals from the plurality of detection elements 122 are electrically combined and input to the readout circuit 222 via the first signal input terminal 120. The signal is converted into digital data via the operational amplifier 154, the sample hold circuit 155, the multiplexer 156, and the A/D converter 157.

The signal read by the readout circuit 222 is detected and processed by the signal processing portion 224. The control circuit 225 determines the presence/absence of radiation irradiation based on the signal from the signal processing portion 224. Upon determining that radiation irradiation exists, a period T2 shown in FIG. 3 starts. During the period T1, to remove a dark current generated in the conversion elements 102, each conversion element 102 can periodically be reset to a constant potential. In this example, the gate control voltages Vg1 to Vgn of the driving lines 104 are sequentially changed to HI to electrically connect the conversion elements 102 to the image signal lines 106 fixed at a constant voltage, thereby preventing the dark current from being accumulated in the conversion elements 102 for a long time. The specific length of the period T1 largely changes depending on the shooting method, conditions, and the like but normally is several sec to several min.

The operation in the period T2 will be described next. The period T2 is the period of radiation irradiation. This period corresponds to, for example, the period after the start of radiation irradiation is detected until the cumulative exposure dose of radiation reaches a dose suitable for imaging. During this period, the gate control voltages Vd1 to Vdn intermittently change to HI, and the switch elements 123 are intermittently set in the ON state. In addition, the gate control voltage Va is set to HI, and the gate control voltages Vb and Vc are set to LO, thereby turning off the switch elements 112 and 118. Electrical connection between the detection signal lines 110 is canceled. The detection elements 122 connected to each detection signal line 110 are electrically connected to one of the second signal input terminals 117. Signals from the detection elements 122 connected to each of the detection signal lines are electrically combined. In the period T2, however, the number of detection elements 122 of signals combined and input to each second signal input terminal 117 is smaller than in the period T1. In this embodiment, all the detection elements 122 are connected to the first signal input terminal 120 in the period T1. On the other hand, in the period T2, the detection elements 122 connected to each detection signal line 110 arranged along a column of pixels are connected to the second signal input terminal 117 corresponding to the detection signal line.

The signals from the detection elements 122 are input to the readout circuit 222 via the second signal input terminal 117 for each detection signal line 110 and converted into digital data via the operational amplifier 150, the sample hold circuit 151, the multiplexer 152, and the A/D converter 153. A detailed description of the circuit arrangement and the processing method after the readout circuit 222 will be omitted. The signal can have any one of the forms of charges, voltage, and current. The plurality of digital signals individually digital-converted by the A/D converter 153 are sent to the control circuit 225 via the signal processing portion 224. The control circuit 225 detects the exposure dose of radiation based on the plurality of digital signals from the readout circuit 222. During the period T2, to accumulate the signals generated in the conversion elements 102 by radiation, the gate control voltages Vg1 to Vgn of the driving lines 104 are set to LO, and the signals generated in the pixels 101 are accumulated in the conversion elements 102. The specific length of the period T2 largely changes depending on the shooting method, conditions, and the like but normally is several hundred μsec to several hundred msec. If the control circuit 225 or the external radiation generator 227 determines to stop radiation irradiation based on the detection result of the exposure dose of radiation by the control circuit 225, the operation transits or is controlled to transit to a period T3 shown in FIG. 3.

The operation in the period T3 will be described finally. The period T3 is the period of reading out image signals accumulated in the pixels 101 and the detecting pixels 121 after the end of radiation irradiation. During this period, the gate control voltages Vd1 to Vdn are set to LO, the gate control voltage Va is set to HI, and the gate control voltages Vb and Vc are set to LO. To prevent the detection signal lines 110 from floating state, the detection signal lines 110 are connected to a fixed potential via the second signal input terminals 117. In addition, to scan the driving lines 104, the gate control voltages Vg1 to Vgn are sequentially set to HI. With this scan, the image signals accumulated in the conversion elements 102 of the pixels 101 and the detecting pixels 121 are transmitted to the readout circuit 222 via the image signal input terminals 107. The signals are used as shot image information used for diagnosis. A detailed description of the circuit arrangement and the processing method after the readout circuit 222 will be omitted. In this embodiment, to attain a predetermined accumulation time in each conversion element 102, the accumulation time from the last scan of the driving lines 104 in the period T1 to the scan in the period T3 is made constant. In FIG. 3, Vg1 is finally set to HI during the period T1. Hence, in the period T3, the scan is started by setting the gate control voltage Vg2 to HI first. This can set a predetermined accumulation time after the gate control voltage Vg is finally set to LO in the period T1 until the gate control voltage Vg is set to HI in the period T3.

In the period T1, since the requirement of a spatial resolution is low or unnecessary, the signals from the detection signal lines 110 to which the plurality of detection elements 122 are connected are combined and read out. It is therefore possible to detect the start of radiation irradiation with a high sensitivity. Additionally, in this embodiment, during the period T1, since the signal can be read using only the operational amplifier 154 and the A/D converter 157 corresponding to one channel without operating the integrated circuit 501, power consumption can be suppressed. In the example, only the operational amplifier 154 and the A/D converter 157 corresponding to one channel are illustrated for the descriptive convenience. However, a plurality of operational amplifiers and A/D converters may be provided. In this case as well, power consumption can sufficiently be suppressed by suppressing the number of channels as compared to the number of detection signal lines.

On the other hand, in the period T2, since the signals from the detection elements can be read out for each second signal input terminal 117 to which the charge signals from the detection elements 122 are connected, the spatial resolution rises as compared to the period T1. During this period, since the integrated circuit 501 including the plurality of operational amplifiers 150, sample hold circuits 151, and multiplexers 152, and the A/D converter 153 operates, power consumption rises as compared to the period T1. However, the power consumption can be suppressed because the period T2 is much shorter than the period T1 in terms of time.

In this embodiment, during the period T1 when a sensitivity is needed, the signals from the detection elements 122 are bundled. During the period T2 when a resolution is needed, the outputs from each detection signal line can be detected. Hence, irradiation can accurately be detected during the period T1. Since the number of signals to be processed during the period T1 can be decreased, it is possible to reduce the scale of the circuit used for processing and reduce power consumption. During the period T2, the radiation dose can be determined by acquiring information of the radiation exposure dose with a high spatial resolution. Hence, a captured image having a high sharpness can be obtained using this.

Second Embodiment (a) Arrangement of Radiation Imaging Apparatus

Figure 6:
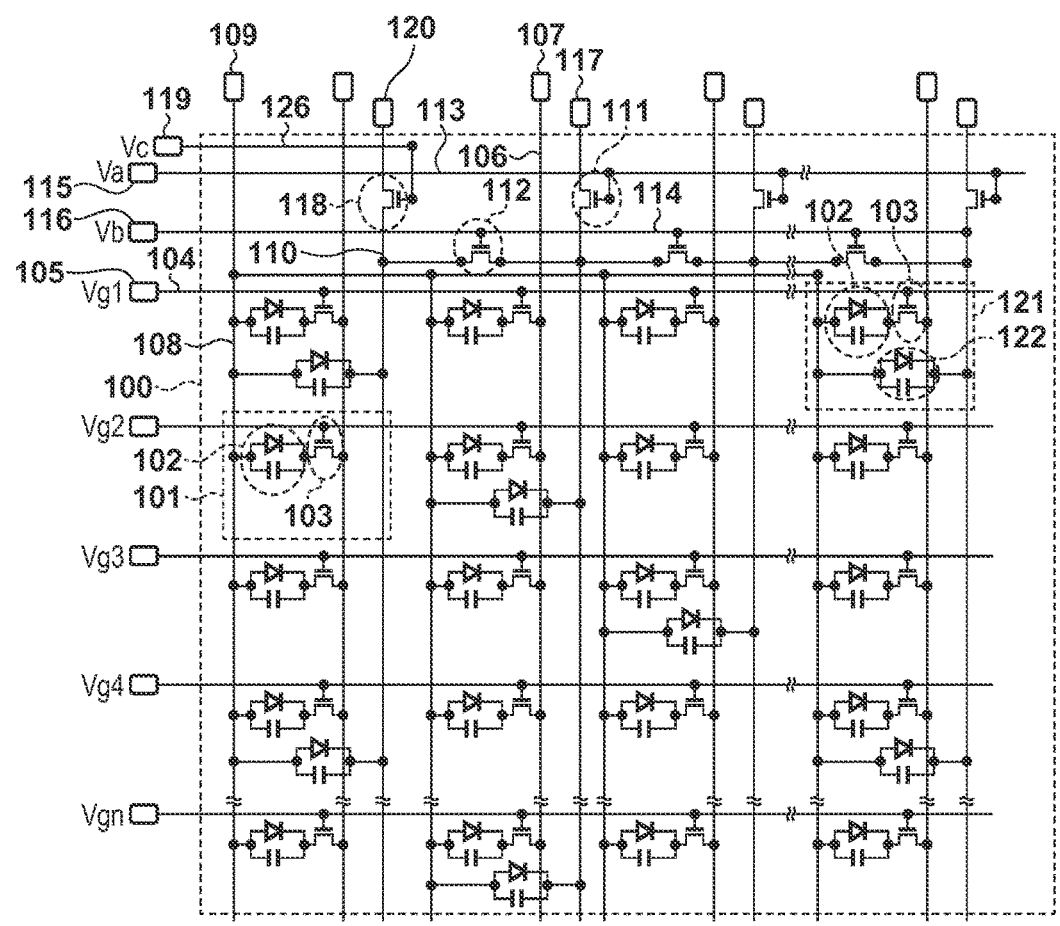
FIG. 6 is a circuit diagram showing an arrangement of a radiation imaging apparatus according to a second embodiment of the present invention.
Figure 8:
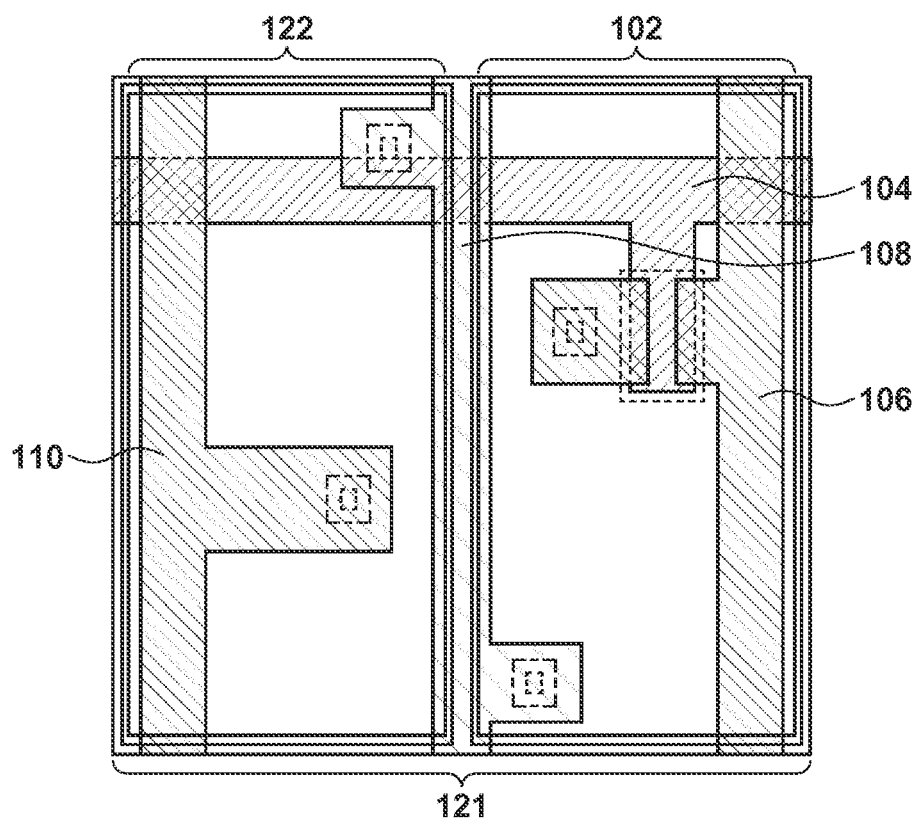
FIG. 8 is a view showing an example of an arrangement of a pixel of the radiation imaging apparatus according to the second embodiment of the present invention.

The same reference numerals as in the first embodiment denote the same parts in the following embodiment, and a description thereof will be omitted. The sensor portion of a radiation imaging apparatus according to the second embodiment of the present invention will be described with reference to FIG. 6. FIG. 6 shows the arrangement of pixels in a support substrate 100. Unlike the first embodiment shown in FIG. 2, a switch element 123 is not connected to a detection element 122 in a detecting pixel 121. Accordingly, a driving line 124 used to drive the switch element 123 is not provided. One or more detection elements 122 are directly connected to each detection signal line 110. When detecting the start of radiation irradiation, a switch element 118 is turned on together with switch elements 112 to extract a bundle of outputs of the detection elements 122 arranged for each column. To extract the outputs from the detection elements 122 for each detection signal line 110, the switch elements 112 are turned off. At this time, the switch element 118 is turned on and functions as a switch element 111. FIG. 8 is a plan view of the detecting pixel 121 according to this embodiment. No switch element is provided in the region of the detection element 122 according to this embodiment. A readout circuit 222 uses the signal from a first signal input terminal 120 to determine the start of radiation irradiation during a period T1, and uses the signals from second signal input terminals to determine the radiation dose during a period T2.

(b) Operation

Figure 7:
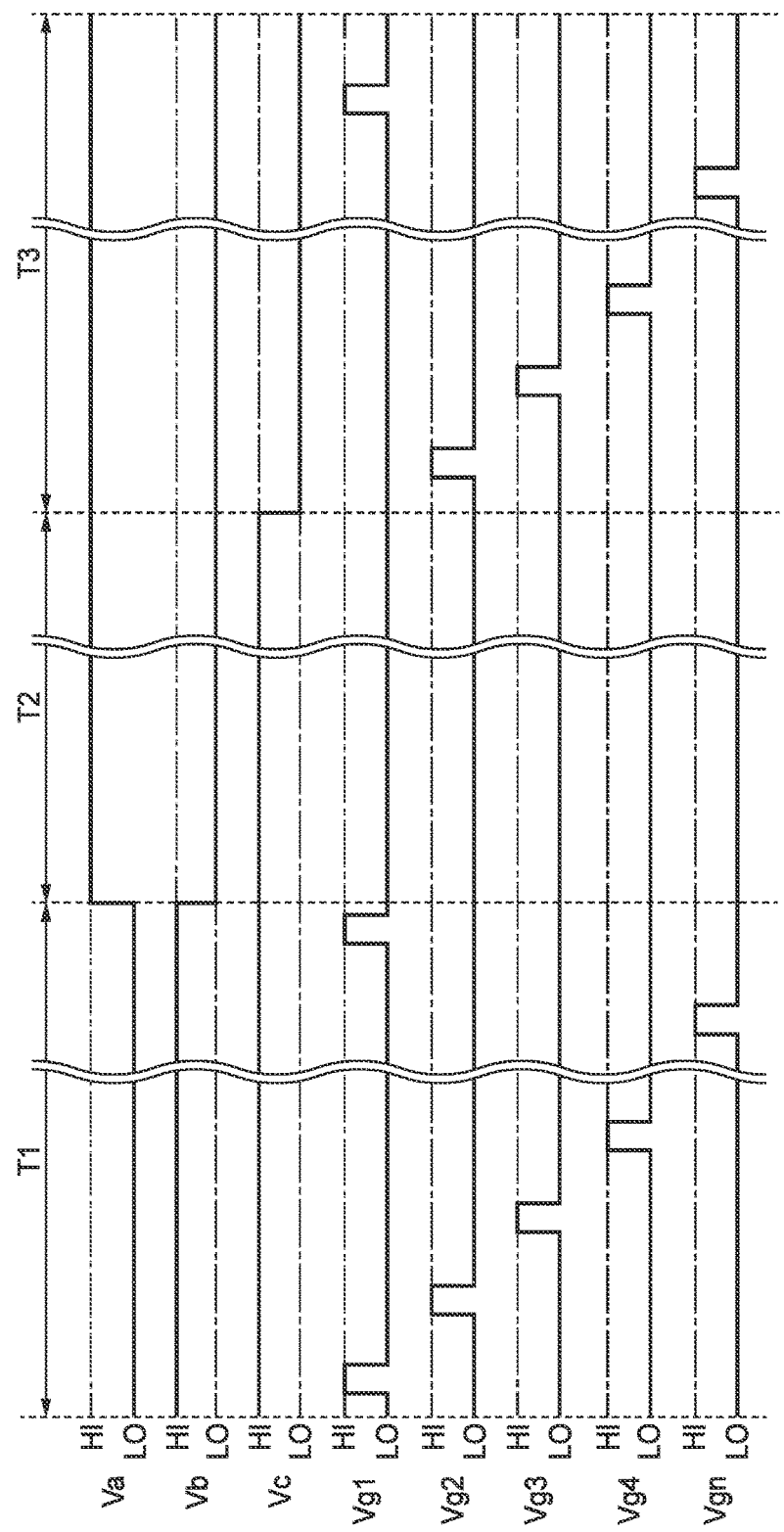
FIG. 7 is a timing chart of the radiation imaging apparatus according to the second embodiment of the present invention.

The operation of the radiation imaging apparatus according to this embodiment will be described next with reference to FIG. 7. Unlike the first embodiment shown in FIG. 2, since the switch element 123 for the detection element is not provided, it is unnecessary to control gate control voltages Vd1 to Vdn. During the period T1, since gate control voltage Vb is HI, the switch elements 112 are turned on, and the adjacent detection signal lines 110 are connected to combine the outputs of the detection elements 122. At this time, since a gate control voltage Vc is HI, the switch element 118 is also ON. The combined output of the signals from the detection elements 122 connected to each detection signal line 110 is output to the first signal input terminal 120 via the switch element 118. Next, during the period T2, the gate control voltage Vb changes to LO, and the gate control voltage Vc changes to HI. As a result, the switch elements 112 are turned off, and the signals from the detection elements 122 are transmitted to the readout circuit 222 via the first signal input terminal 120 and second signal input terminals 117 and used to determine the radiation exposure dose. At this time, the first signal input terminal 120 outputs the signals of the detection elements from the detection signal line, like the second signal input terminals 117. According to this arrangement, during the period T1, the signals from the detection elements are bundled to detect the start of radiation irradiation, as in the first embodiment. It is therefore possible to sensitively perform the detection. During the period T2, the signals from the detection signal lines 110 are provided to the readout circuit 222 without being combined. It is therefore possible to determine the radiation dose on a region basis, make the spatial resolution higher than in the period T1, and provide a captured image having a high sharpness. In addition, since the scale of the circuit operating in the period T1 can be suppressed, power consumption in the period T1 can be reduced. Furthermore, when the first signal input terminal 120 is used as the second signal input terminal 117, the number of connection terminals can be suppressed. It is therefore possible to reduce the scale of the input circuit.

Third Embodiment (a) Arrangement of Radiation Imaging Apparatus

Figure 9:
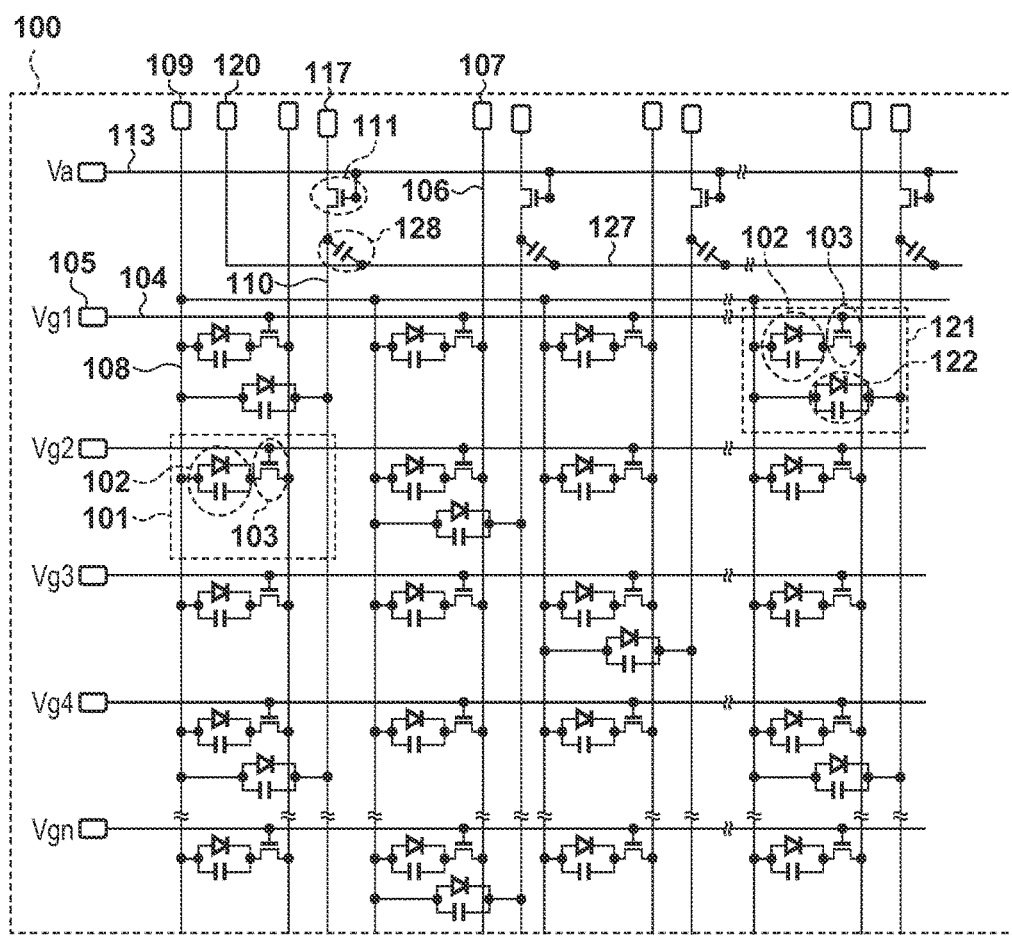
FIG. 9 is a circuit diagram showing an arrangement of a radiation imaging apparatus according to the third embodiment of the present invention.

The sensor portion of a radiation imaging apparatus according to this embodiment will be described with reference to FIG. 9. FIG. 9 shows pixels arranged in a support substrate 100. Unlike the first embodiment shown in FIG. 2, a switch element 123 for a detection element is not provided in a detecting pixel 121. Accordingly, a driving line 124 is not provided. In addition, switch elements 112 and 118 and driving lines 114 and 126 are not provided. A signal line 127 is connected to a first signal input terminal 120. The signal line 127 is connected to each detection signal line 110 via a capacitor portion 128. The capacitor portions 128 function as a combining portion that combines the signals of the detection signal lines 110. FIG. 11 shows a modification of this embodiment in which the first electrode of the detection element 122 in each detecting pixel 121 is connected to an image signal line 106, and the image signal line 106 functions as the detection signal line 110. Similarly, an image signal input terminal 107 of a readout circuit 222 functions as a second signal input terminal 117. A readout circuit 222 uses the signal from the first signal input terminal 120 to determine the start of radiation irradiation during a period T1, and uses the signals from the image signal input terminals 107 to detect the radiation dose during a period T2. In a period T3, the readout circuit 222 processes the signal from each image signal input terminal 107 as an imaging signal.

(b) Operation

Figure 10:
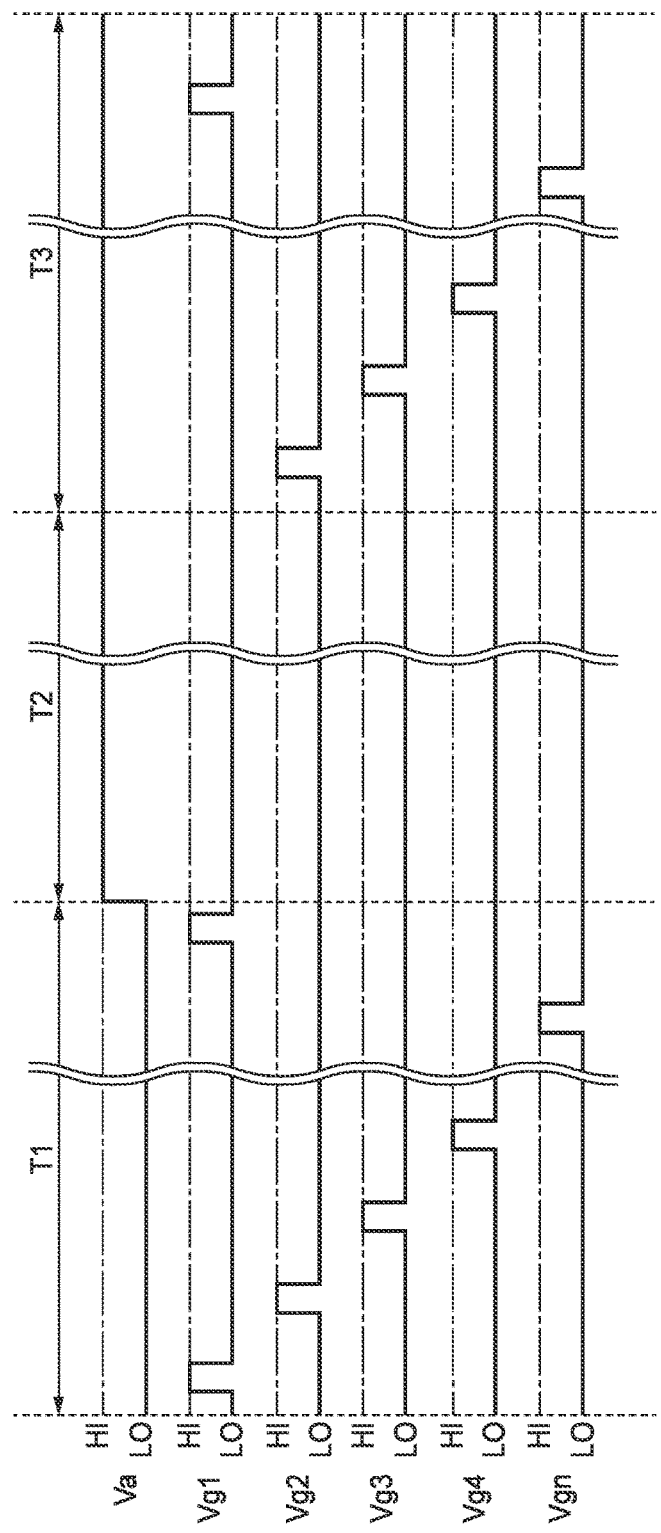
FIG. 10 is a timing chart of the radiation imaging apparatus according to the third embodiment of the present invention.

The operation of the radiation imaging apparatus according to this embodiment will be described with reference to FIG. 10. During the period T1, a gate control voltage Va is set to LO, switch elements 111 between the second signal input terminals 117 and the detection signal lines 110 are turned off, and each detection signal line 110 floats. Hence, when signal charges are generated in the detection element 122, the potential of each detection signal line 110 fluctuates. The potential fluctuation of the plurality of detection signal lines 110 is transmitted to the signal line 127 capacitively coupled via the capacitor portions 128 between the plurality of signal lines as a change in the potential caused by the signal charges from the plurality of detection elements 122. In the period T2, the gate control voltage Va is set to HI to turn on the switch elements 111. The readout circuit 222 reads out the signals from the detection elements 122 via the second signal input terminals 117 to determine the radiation dose.

According to this arrangement, during the period T1, the signals from the detection elements 122 can be read out as a change in the voltage. Hence, charge movement in the readout does not occur. The charges used to determine the presence/absence of radiation irradiation during the period T1 can also be used to detect the radiation exposure dose during the period T2. The detection accuracy is improved, and an image having a high sharpness can be obtained.

Additionally, in the form shown in FIG. 11, since the detection signal and the image signal are read out using the same signal input terminal, the number of input terminals of the readout circuit 222 can be decreased. This is advantageous in reducing the scale and power consumption of the readout circuit 222.

Fourth Embodiment (a) Arrangement of Radiation Imaging Apparatus

Figure 12:
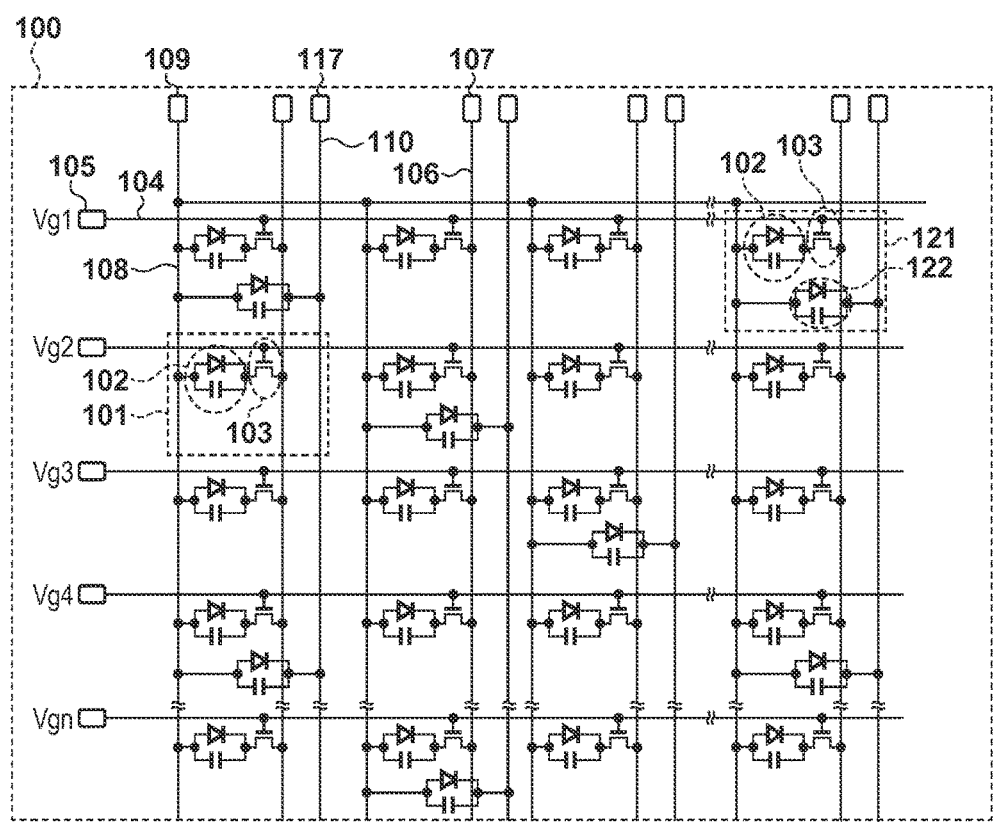
FIG. 12 is a circuit diagram showing an arrangement of a radiation imaging apparatus according to a fourth embodiment of the present invention.

A radiation imaging apparatus according to this embodiment will be described with reference to FIG. 12. FIG. 12 shows the arrangement of a sensor portion on a support substrate 100. Unlike the first embodiment shown in FIG. 2, a switch element 123 for a detection element is not provided in a detecting pixel 121. Accordingly, a driving line 124 is not provided. In addition, switch elements 111, 112, and 118, driving lines 113, 114, and 126, and a first signal input terminal 120 are not provided. The radiation imaging apparatus according to this embodiment is configured to detect radiation irradiation by monitoring a change in a current that flows from a power supply circuit 226 to a bias line 108. The bias current is monitored by causing the power supply circuit 226 to A/D-convert the bias current and send the converted data to a control circuit 225. In this case, the power supply circuit 226 also functions as a readout circuit 222.

If a detection element 122 to which the voltage is applied via a bias power supply terminal 109 and a bias line 108 is irradiated with radiation, signal charges are generated in the detection element 122. The generated signal charges flow to the bias power supply terminal 109 via the bias line 108. Alternatively, since a potential fluctuation occurs in a conversion element 102 as well due to the charge generation, the potential fluctuation is transmitted to the bias line 108 via a parasitic capacitance (not shown) and flows to the bias power supply terminal 109. The control circuit 225 determines irradiation based on the bias current monitoring by the power supply circuit 226, and sends a control signal to a driving circuit 221 and the readout circuit 222.

(b) Operation

Figure 13:
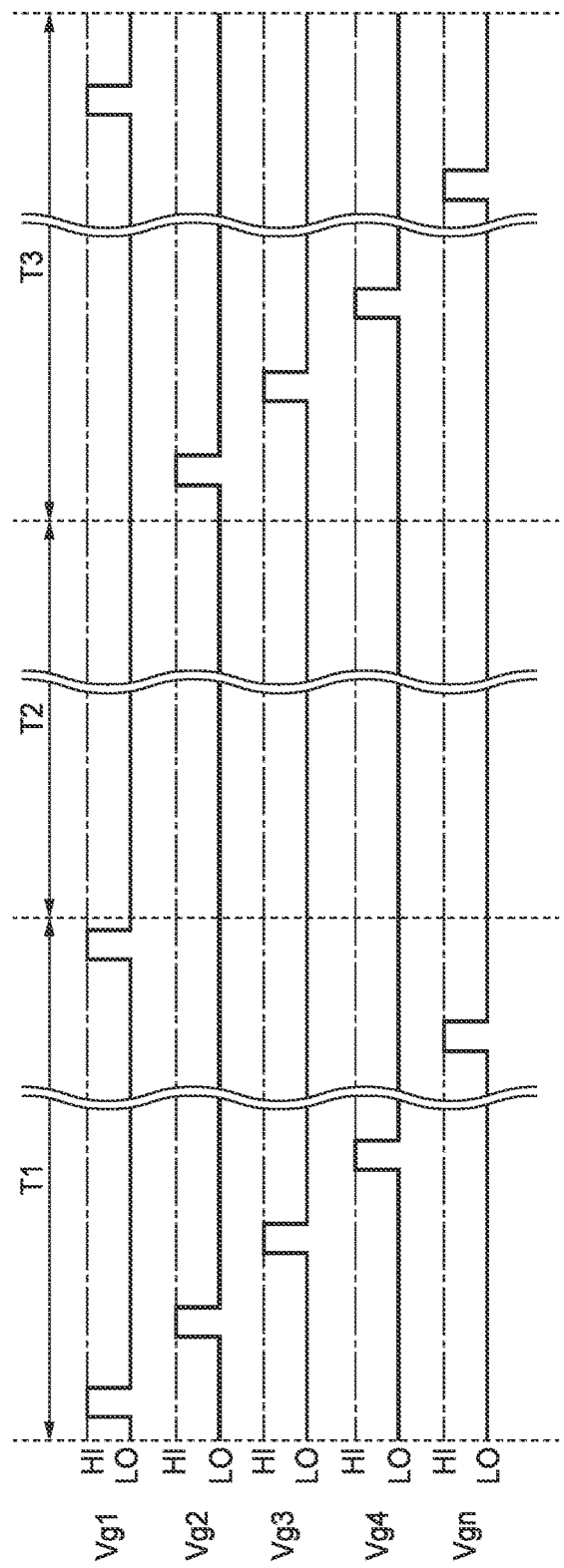
FIG. 13 is a timing chart of the radiation imaging apparatus according to the fourth embodiment of the present invention.

The operation of the radiation imaging apparatus according to this embodiment will be described with reference to FIG. 13. In this embodiment, during a period T1, the current flowing to the bias line 108 is monitored, thereby determining the presence/absence of radiation irradiation. During the period T1, gate control voltages Vg1 to Vgn periodically change to HI to reset a dark current. When radiation irradiation starts, the outputs of the detection elements 122 and the conversion elements 102 change. The change affects the bias line, and the bias current changes. The power supply circuit 226 monitors the change in the bias current. If a change occurs, it is determined that irradiation has started. During a period T2, the outputs of the detection elements 122 are input from second signal input terminals 117 to the readout circuit 222, and the exposure dose is measured. When a predetermined radiation dose is detected, switch elements 103 are controlled to start reading out image signals from the conversion elements 102 in a period T3.

According to this arrangement, during the period T1, it is possible to bundle the signals from many detection elements 122 and detect radiation using the current flowing to the bias line 108. During the period T2, since information of a radiation exposure dose with a high spatial resolution can be acquired, an image having a high sharpness can be obtained. In addition, since the number of switch elements can be decreased, and wiring of driving lines can be omitted, power consumption can advantageously be reduced.

Fifth Embodiment (a) Arrangement of Radiation Imaging Apparatus

Figure 14:
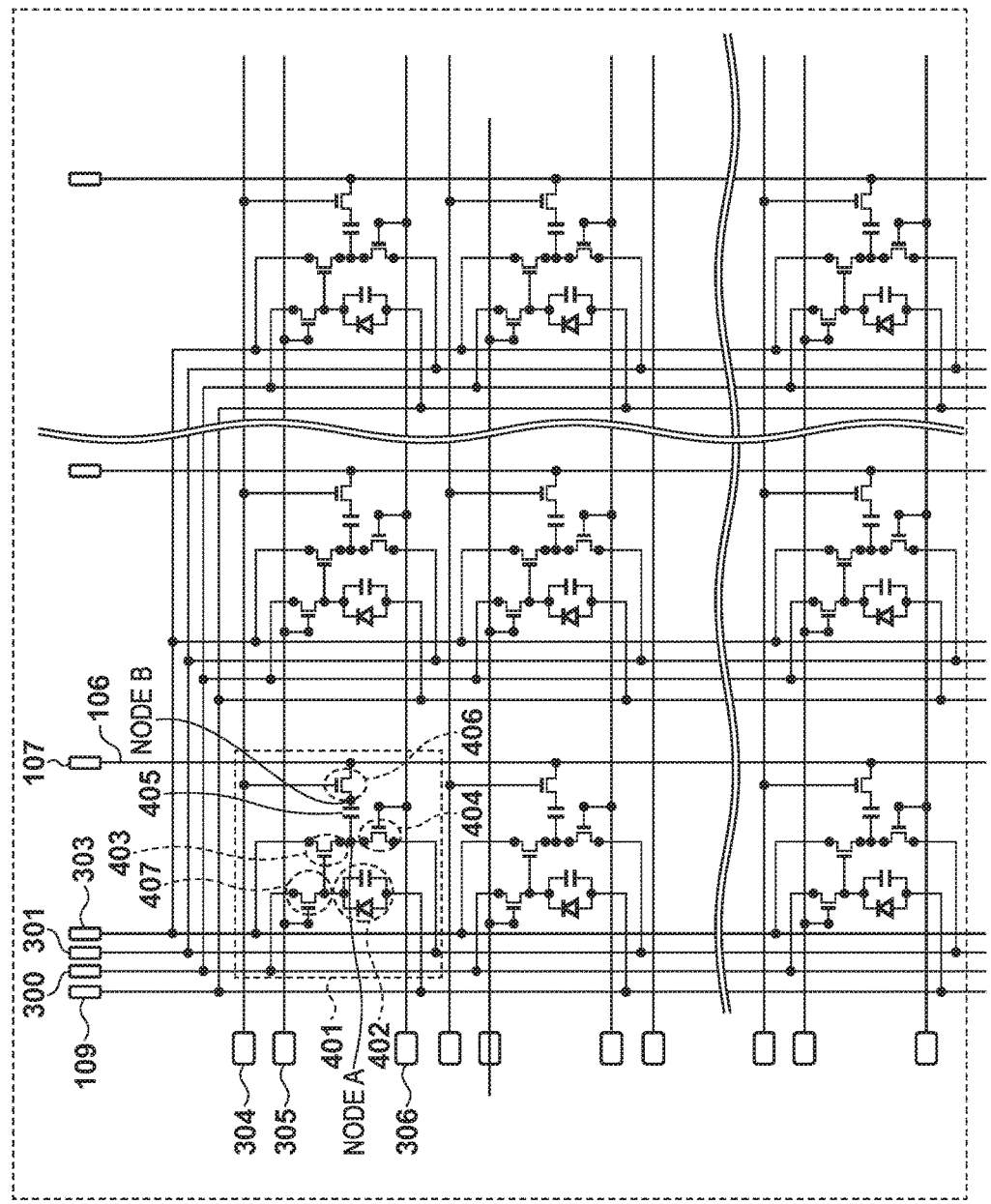
FIG. 14 is a circuit diagram showing an arrangement of a radiation imaging apparatus according to the fifth embodiment of the present invention.

The sensor portion of a radiation imaging apparatus according to this embodiment will be described with reference to FIG. 14. The radiation imaging apparatus according to this embodiment includes a sensor portion including a plurality of pixels 401 arranged in an array on a support substrate 100. The pixel 401 is configured to output an electrical signal corresponding to radiation or light, and includes a conversion element 402 that converts radiation or light into charges, a reset switch element 407, a source follower 403, a load switch element 404, an internal capacitor 405, and a pixel selection switch 406. A bias power supply terminal 109 is electrically connected to a second electrode of the conversion element 402. A first electrode of the conversion element 402 is connected to the control electrode of the source follower 403 and a first main electrode of the reset switch element 407. The source follower 403 is an amplification MOS transistor that outputs a signal corresponding to the charges from the conversion element to an image signal line 106.

A second main electrode of the reset switch element 407 is electrically connected to a reset potential supply terminal 300, and a reset voltage is applied to the second main electrode via the reset potential supply terminal 300. The control electrode of the reset switch element 407 is electrically connected to a pixel reset switch terminal 305, and a potential Vres to ON/OFF-control the reset switch element 407 is supplied to the control electrode via the pixel reset switch terminal 305. The first main electrode of the source follower 403 is electrically connected to a positive potential supply terminal 303, and a power supply voltage is applied to the first main electrode. The second main electrode of the source follower 403 is connected to the first main electrode of the load switch element 404 and a first electrode of the internal capacitor 405. A node to which the second main electrode of the source follower 403, a first main electrode of the load switch element 404, and a first electrode of the internal capacitor 405 are connected will be referred to as a node A hereinafter for the descriptive convenience. The first main electrode of the pixel selection switch 406 is connected to a second electrode of the internal capacitor 405. A node to which the second electrode of the internal capacitor 405 and the first main electrode of the pixel selection switch 406 are connected will be referred to as a node B hereinafter for the descriptive convenience.

A second main electrode of the pixel selection switch 406 is connected to the image signal line 106. A control electrode of the pixel selection switch 406 is electrically connected to a pixel selection switch terminal 304, and a potential Vsel to ON/OFF-control the pixel selection switch 406 is supplied to the control electrode via the pixel selection switch terminal 304. The second main electrode of the load switch element 404 is connected to a GND terminal 301, and a GND potential is applied to the second main electrode. The control electrode of the load switch element 404 is connected to a load switch terminal 306, and a potential Vload to ON/OFF-control the switch is supplied to the control electrode via the load switch terminal 306. The image signal line 106 is connected to an image signal input terminal 107.

In the arrangement of the radiation imaging apparatus according to this embodiment, a driving circuit 221 is connected to the pixel selection switch terminal 304, the pixel reset switch terminal 305, and the load switch terminal 306, and supplies Vres, Vsel, and Vload to them, respectively. A power supply circuit 226 supplies a bias potential to the bias power supply terminal 109. The power supply circuit 226 is also connected to the reset potential supply terminal 300, the positive potential supply terminal 303, and the GND terminal 301 and supplies potentials to them. The power supply circuit 226 applies a reset potential to the reset potential supply terminal 300, and also monitors the amount of the current supplied from the bias power supply. A control circuit 225 sends a control signal to the driving circuit 221 and a readout circuit 222 based on the result of current amount monitoring by the power supply circuit 226.

(b) Operation

Figure 15:
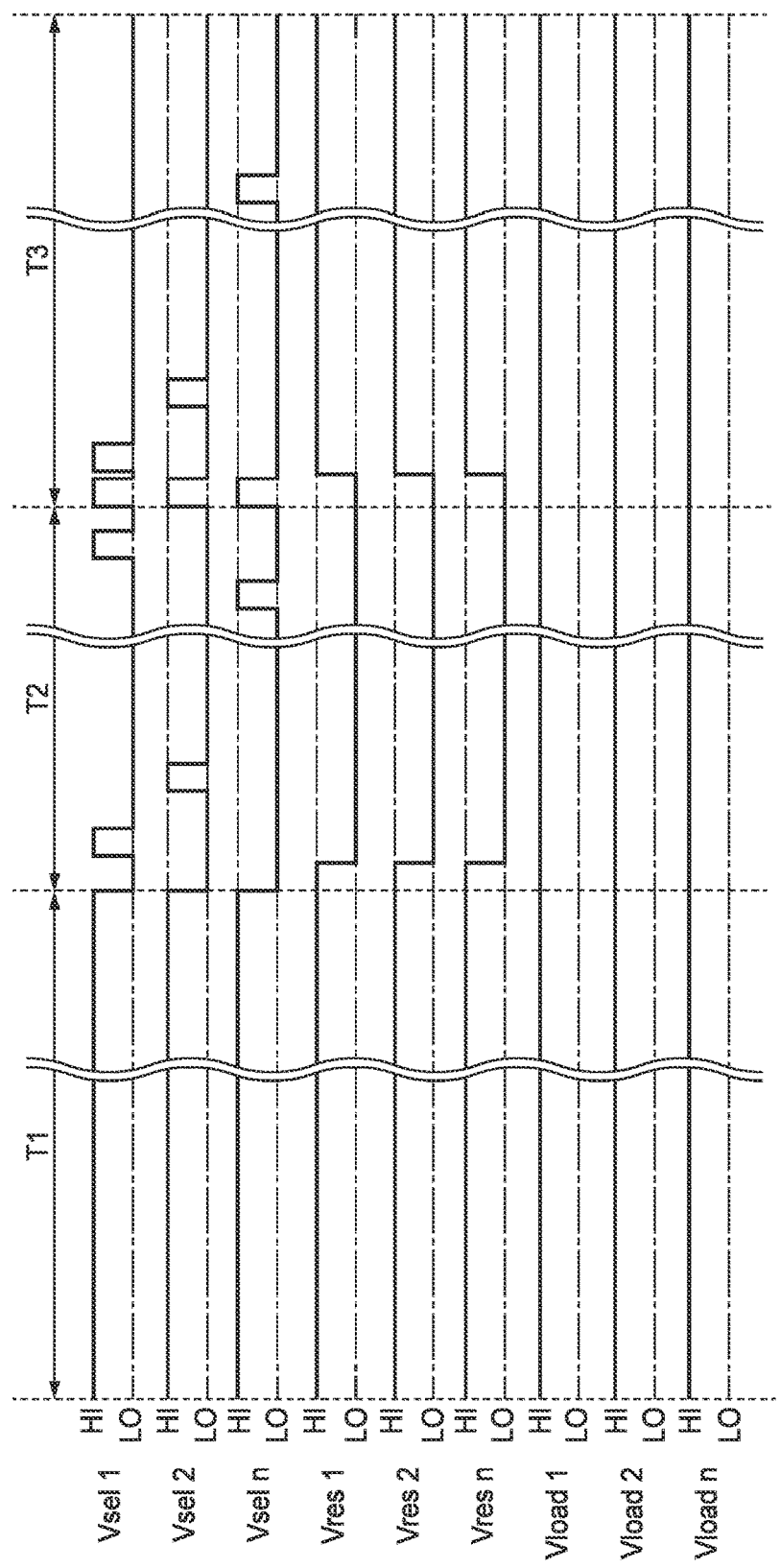
FIG. 15 is a timing chart of the radiation imaging apparatus according to the fifth embodiment of the present invention.

The operation of the radiation imaging apparatus according to this embodiment will be described with reference to FIG. 15. Let Vsel1 to Vseln, Vres1 to Vresn, and Vload1 to Vloadn be the voltages applied to the pixel selection switch terminals 304, the pixel reset switch terminals 305, and the load switch terminals 306 of the first to nth rows. Within the scope of the description of this embodiment, the voltages Vload1 to Vloadn are always HI. In this embodiment, the signals from the conversion elements 402 are used to obtain a captured image signal and also used to determine the presence/absence of radiation irradiation and determine the radiation exposure dose.

The operation in a period T1 shown in FIG. 15 will be described first. The period T1 is a period to detect the presence/absence of radiation irradiation. During this period, the voltages Vres1 to Vresn are set to HI, and the node A is always fixed to the reset voltage supplied from the reset potential supply terminal 300. At this time, changes in the signals from the plurality of conversion elements 402 are transmitted to the power supply circuit 226 via the reset potential supply terminal 300 and the bias power supply terminal 109. The control circuit 225 determines the presence/absence of radiation irradiation based on detection of a change in the current of the bias power supply by the power supply circuit 226. If the control circuit 225 determines that radiation irradiation exists, a period T2 shown in FIG. 15 starts. During the period T1, the voltages Vsel1 to Vseln are set to HI, thereby turning on the pixel selection switches 406 and supplying a fixed potential from the image signal input terminals 107 to the nodes B.

The operation in a period T2 will be described next. The period T2 is the period of radiation irradiation. First, the voltages Vsel1 to Vseln are set to LO to turn off the pixel selection switches 406 and make the nodes B into floating state. The voltages Vres1 to Vresn are set to LO to turn off the reset switch elements 407 to set the pixels 401 in a state capable of accumulating charges. When charges corresponding to the radiation exposure dose are generated, a potential corresponding to the charges is generated in each node A. A change in the potential of the node A appears in the node B via the internal capacitor 405 set in the floating state.

Next, the voltages Vsel1 to Vseln are sequentially set to HI, and the pixel selection switch terminals 304 are sequentially repetitively scanned on a row basis. A change in the potential that has occurred in the node B of each pixel 401 sequentially appears in the readout circuit 222 via the image signal line 106 and the image signal input terminal 107. Using this signal, the control circuit 225 detects the exposure dose of radiation that has entered each pixel 401. In FIG. 15, the voltages are set to HI in the order of Vsel1, Vsel2, and Vseln. However, the order may be changed. The voltages may be applied to repetitively turn on only the pixel selection switches of specific pixels. A change in the potential is input to the image signal input terminal 107 of the readout circuit 222. During the period T2, the exposure dose is determined based on the potential read out by the readout circuit 222, and the control circuit 225 is controlled to stop radiation irradiation. Alternatively, the control circuit may output a signal to an external radiation generator, and the external radiation generator may determine whether to stop irradiation. If the radiation irradiation stops, the operation transits to a period T3 shown in FIG. 15, or the external radiation generator controls to make the radiation imaging apparatus transit to the period T3.

Finally, the operation in the period T3 to read out the signal accumulated in the pixel 401 by radiation after the end of radiation irradiation will be described. During this period, first, the voltages Vsel1 to Vseln are set to HI. Each node B is thus fixed to the potential of the image signal input terminal 107, and a potential difference corresponding to the cumulative exposure dose of radiation until the stop of irradiation appears between the electrodes of the internal capacitor 405 via the source follower. Next, the voltages Vsel1 to Vseln are set to LO to make the node B float, and in this state, the voltages Vres1 to Vresn are set to HI. The node A of the internal capacitor 405 changes to the reset potential, and the node B is charged with a voltage corresponding to the cumulative exposure dose of radiation. Finally, the voltages Vsel1 to Vseln are sequentially set to HI. Charges corresponding to the cumulative exposure dose of radiation that has entered each pixel 401 flow to the readout circuit 222 on a row basis via the image signal input terminal 107. This signal is used as shot image information for diagnosis.

According to this arrangement, since the start of radiation irradiation in the period T1 is determined by bundling a number of outputs from the plurality of pixels 401 connected to the reset potential supply terminal 300 and the bias power supply terminal 109, the detection sensitivity can be improved. On the other hand, during the period T2, information of radiation exposure dose can be acquired and processed on a conversion element basis in a state where a satisfactory spatial resolution is attained. It is therefore possible to provide a captured image having a high sharpness.

Sixth Embodiment

Figure 16:
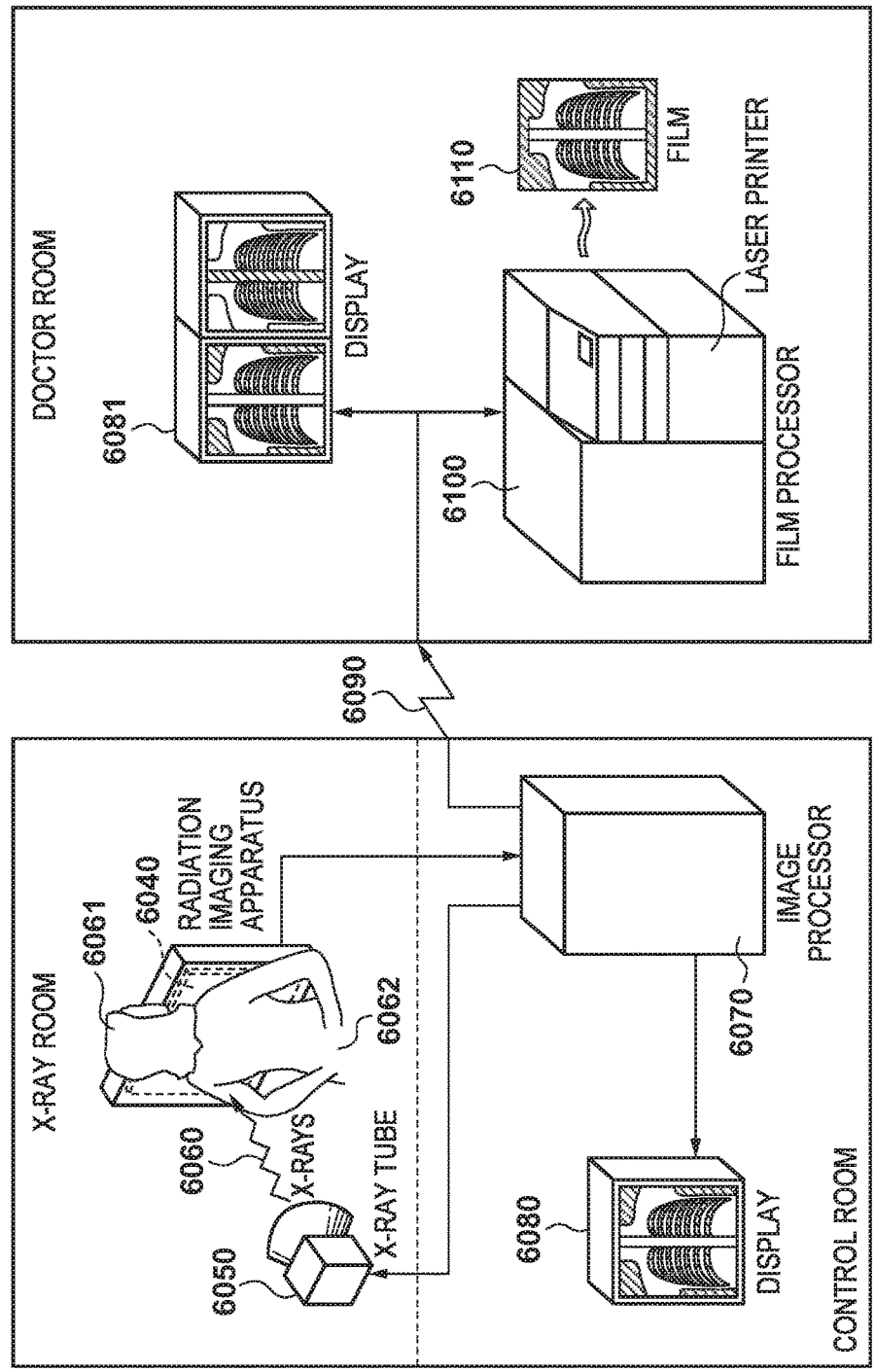
FIG. 16 is a view showing an example of an arrangement of a radiation detection system.

An example of application to a radiation detection system using a radiation imaging apparatus according to the present invention will be described next with reference to FIG. 16. X-rays 6060 generated by an X-ray tube 6050 that is a radiation source for generating radiation are transmitted through a chest 6062 of a patient or subject 6061 and enter an imaging apparatus 6040 according to the present invention. The X-rays that have entered include information about the inside of the body of the patient 6061. If a method of converting X-rays into light by a scintillator is employed, light corresponding to the X-rays that have entered is photoelectrically converted by a photoelectric conversion element, thereby obtaining electrical information. This information is converted into digital data and processed by an image processor 6070 serving as a signal processing means. The data can be observed on a display 6080 serving as a display means in the control room.

This information can also be transferred to a remote site by a transmission processing means such as a telephone line 6090, and displayed on a display 6081 serving as a display means in a doctor room of another place or saved in a recording medium such as an optical disk so that a doctor in the remote site can make a diagnosis. The information can also be recorded in a film 6110 serving as a recording medium by a film processor 6100 serving as a recording means.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-164530, filed Aug. 12, 2014, which is hereby incorporated by reference herein in its entirety.

What is claimed is:

1. A radiation imaging apparatus for determining the presence or absence of radiation irradiation and determining a radiation dose, said radiation imaging apparatus comprising:
   a sensor portion including a pixel array configured to acquire an image signal indicating detected radiation, and a plurality of detection elements arranged in the pixel array and configured to detect the radiation; and
   a circuit configured to read out at least the image signal from the sensor portion, wherein
   the circuit generates a first signal for determining the presence or absence of radiation irradiation, and a second signal for determining the radiation dose,
   the first signal corresponds to a combination of signals from detection elements of a first subset of the plurality of detection elements provided by an electrical connection to the circuit collectively, and the second signal corresponds to a combination of signals from detection elements of a second subset of the plurality of detection elements provided by an electrical connection to the circuit collectively, and
   the number of detection elements of the first subset is greater than the number of detection elements of the second subset.

2. The apparatus according to claim 1, wherein the sensor portion further includes a plurality of detection signal lines to which the detection elements are connected, and a combining portion configured to combine signals of the plurality of detection signal lines by electric connection to the circuit collectively, and
   the plurality of detection elements are connected to any one of the plurality of detection signal lines.

3. The apparatus according to claim 2, wherein the combining portion includes switch elements operable to connect the plurality of detection signal lines to the circuit.

4. The apparatus according to claim 2, wherein the circuit includes a first signal processing circuit for processing the first signal, and a second signal processing circuit for processing the second signal, and
   the combining portion includes an element configured to capacitively couple the plurality of detection signal lines with the first signal processing circuit.

5. The apparatus according to claim 1, wherein the circuit further includes a power supply circuit to apply a bias voltage to the plurality of detection elements via bias line, the power supply monitors a current flowing in the bias line, the presence or absence of radiation irradiation is determined based on the first signal which is based on a change in the current flowing in the bias line monitored by the power supply, and the radiation dose is determined based on the second signal which is read out via at least one of an image signal line and the detection signal line.

6. The apparatus according to claim 2, wherein the detection element comprises a conversion element configured to generate charges corresponding to the radiation, an amplification MOS transistor arranged to output a signal corresponding to the charges from the conversion element to the detection signal line, and a reset switch arranged to reset the conversion element.

7. The apparatus according to claim 6, wherein the detection element is arranged to output the image signal corresponding to the radiation to the detection signal line.

8. The apparatus according to claim 1, wherein the circuit further comprises:

a first signal processing circuit configured to combine and process the first signal; and a second signal processing circuit configured to process the second signal, wherein during determining the presence or absence of radiation irradiation, the first signal processing circuit is operated, and operation of the second signal processing circuit is stopped, and during determining the radiation dose, the second signal processing circuit is operated.

9. A radiation detection system comprising:

a radiation source configured to generate radiation; and a radiation imaging apparatus defined in claim 1.

* * * * *